United States Patent [19]
Shieh

[11] Patent Number: 5,883,340
[45] Date of Patent: Mar. 16, 1999

[54] STETHOSCOPE

[76] Inventor: Woei-Kang Shieh, No. 63, Yung-Ping Street, Lu-Chu, Taipei, Hsien, Taiwan

[21] Appl. No.: 905,663

[22] Filed: Aug. 4, 1997

[51] Int. Cl.$^6$ ........................................................ A61B 7/02
[52] U.S. Cl. ................................................................. 181/131
[58] Field of Search ..................................... 181/131, 137; 381/67

[56] References Cited

U.S. PATENT DOCUMENTS

| | | | |
|---|---|---|---|
| 3,168,160 | 2/1965 | Littmann et al. | 181/135 |
| 4,200,169 | 4/1980 | MacDonald, III et al. | 181/131 |
| 5,288,954 | 2/1994 | Peart | 181/131 |

Primary Examiner—Khanh Dang
Attorney, Agent, or Firm—Townsend and Townsend and Crew LLP

[57] ABSTRACT

A stethoscope includes a Y-shaped metal tube, a pair of binaural tubes, a pair of resilient tubes and a Y-shaped rubber tube. The metal tube has a main tube section and two branch tube sections connected to the main tube section. Each of the resilient tubes has two opposite ends which connect a distal end of a respective one of the branch tube sections to a distal end portion of a respective one of the binaural tubes. The rubber tube has a first tube section which confines the main tube section and two second tube sections connected to the first tube section. Each of the second tube sections is sleeved onto a respective one of the branch tube sections, a respective one of the resilient tubes and the distal end portion of a respective one of the binaural tubes in order to conceal the Y-shaped metal tube and the resilient tubes in the Y-shaped rubber tube.

3 Claims, 6 Drawing Sheets

STETHOSCOPE

BACKGROUND OF THE INVENTION

1. Field of the Invention

This invention relates to a stethoscope, more particularly to a stethoscope which has a pair of binaural tubes that can apply an optimum clamping force onto the user's ears and which produces a minimum sound distortion when in use.

2. Description of the Related Art

Referring to FIGS. 1 and 2, a conventional stethoscope is shown to comprise a pair of binaural tubes 10, a Y-shaped rubber tube 13 having a first tube section 16 and two second tube sections 14 connected to the first tube section 16, and a U-shaped resilient member 12. The first tube section 16 has a lower end which is connected to a chest piece (not shown). Each of the second tube sections 14 has an upper end which is connected to a lower end of a respective one of the binaural tubes 10. The U-shaped resilient member 12 has two upper ends engaging respectively the binaural tubes 10 in order to apply a clamping force onto the user's ears when the stethoscope is in use.

Some of the drawbacks of the conventional stethoscope are as follows:

1. The clamping force is hardly maintained at a constant, proper amount after the stethoscope has been in use for a period of time. Therefore, the user must adjust the clamping force several times by bending the U-shaped resilient member 12. Control of the adjustment of the clamping force applied by the U-shaped resilient member 12 to an optimum amount is difficult to conduct. If the clamping force is too large, the user's ears may feel uncomfortable. On the contrary, if the clamping force is too small, the binaural tubes 10 are likely to slip from the user's ears while the stethoscope is in use.

2. The sound is transmitted from the chest piece to the user's ears through the rubber tube 13, which produces high sound distortion.

3. The sharp edges of the U-shaped resilient member 12 may injure the user's hands.

Referring to FIGS. 3 and 4, another conventional stethoscope is shown to comprise a pair of binaural tubes 11, a Y-shaped rubber tube 18 and a U-shaped resilient member 17. The structures of the binaural tube 11, the rubber tube 18 and the U-shaped resilient member 17 are similar to those of the aforementioned conventional stethoscope. However, the U-shaped resilient member 17 is disposed within the rubber tube 18 in order to protect the user from being injured by the U-shaped resilient member 17. Since the U-shaped resilient member 17 will reduce the sound transmission efficiency, a sound divider 19 is mounted in the intersection point of the rubber tube 17 in order to enhance the sound transmission efficiency. However, sound distortion still occurs during the transmission of sound in the stethoscope. In addition, the problem of adjustment of the clamping force of the binaural tubes 11 still exists in this stethoscope.

SUMMARY OF THE INVENTION

It is an object of the present invention to provide a stethoscope which has a pair of binaural tubes that can apply an optimum clamping force onto the user's ears and which produces a minimum sound distortion when in use.

According to the present invention, a stethoscope comprises a Y-shaped metal tube, a pair of binaural tubes, a pair of resilient tubes and a Y-shaped rubber tube. The metal tube has a main tube section and two branch tube sections connected to the main tube section. Each of the resilient tubes has two opposite ends which connect a distal end of a respective one of the branch tube sections to a distal end portion of a respective one of the binaural tubes. The rubber tube has a first tube section sleeved onto the main tube section and two second tube sections connected to the first tube section. Each of the second tube sections is sleeved onto a respective one of the branch tube sections, a respective one of the resilient tubes and a respective one of the binaural tubes in order to conceal the Y-shaped metal tube and the resilient tubes in the Y-shaped rubber tube.

Preferably, each of the resilient tubes is formed as a coiled spring which has a plurality of coils that are close to one another.

BRIEF DESCRIPTION OF THE DRAWINGS

Other features and advantages of this invention will become apparent in the following detailed description of the preferred embodiment of this invention with reference to the accompanying drawings, in which.

DETAILED DESCRIPTION OF THE PREFERRED EMBODIMENT

Figure 1:
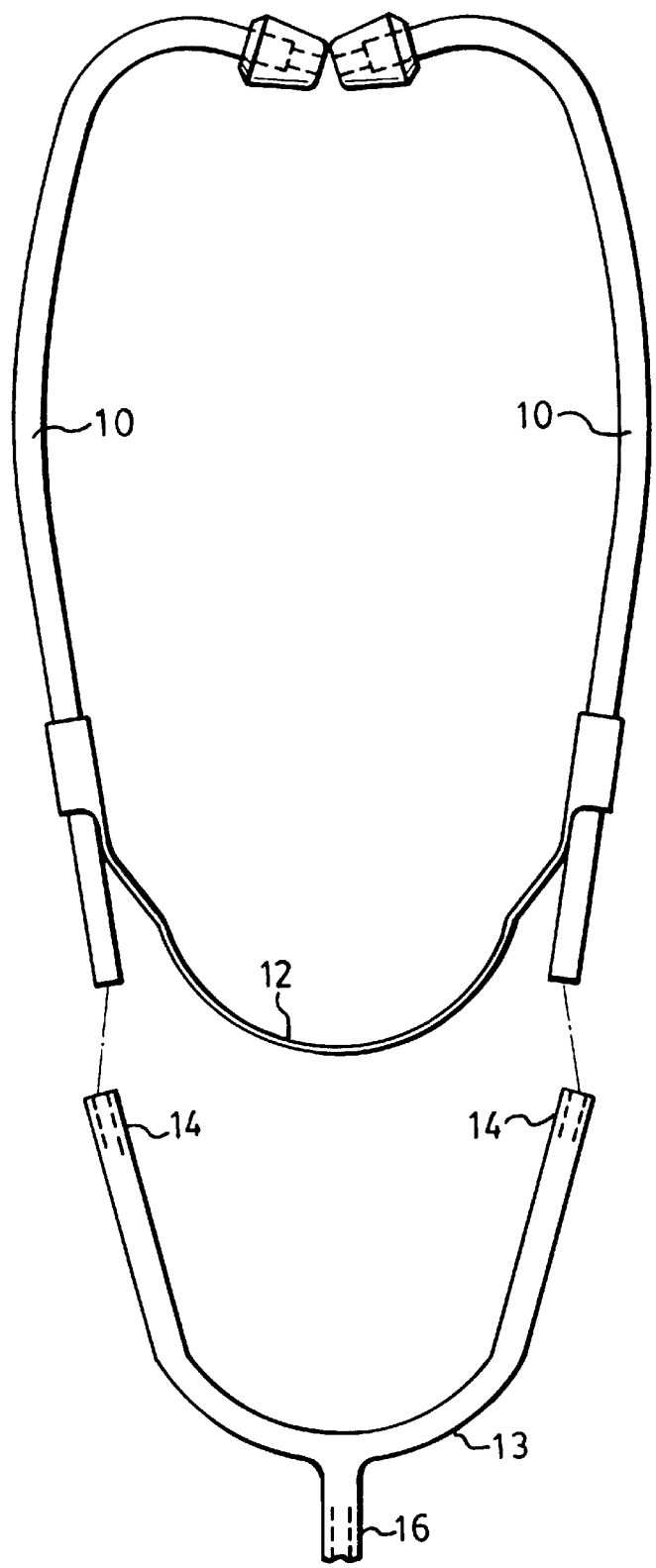
FIG. 1 is an exploded view of a conventional stethoscope.
Figure 2:
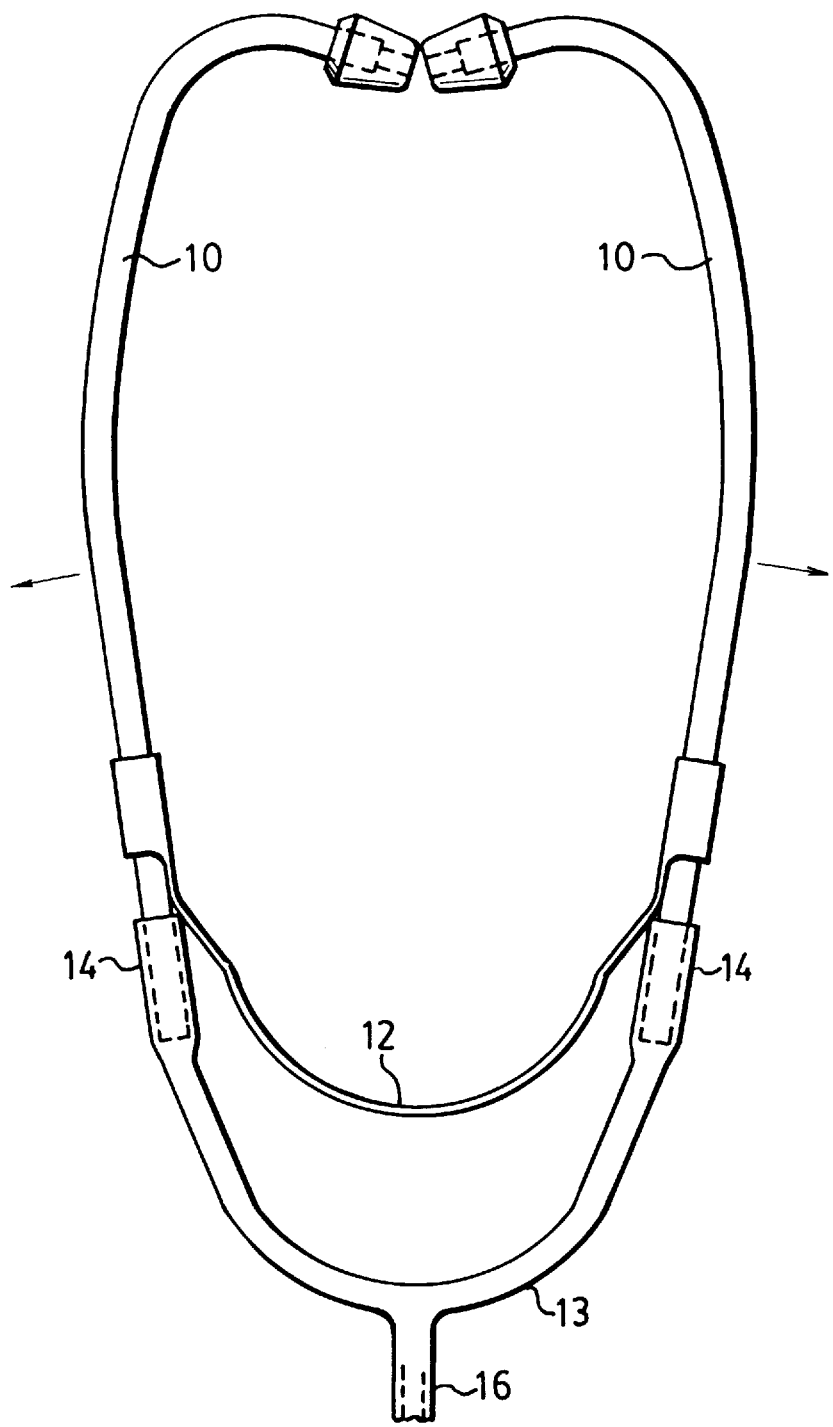
FIG. 2 is a schematic view of the conventional stethoscope of FIG. 1.
Figure 3:
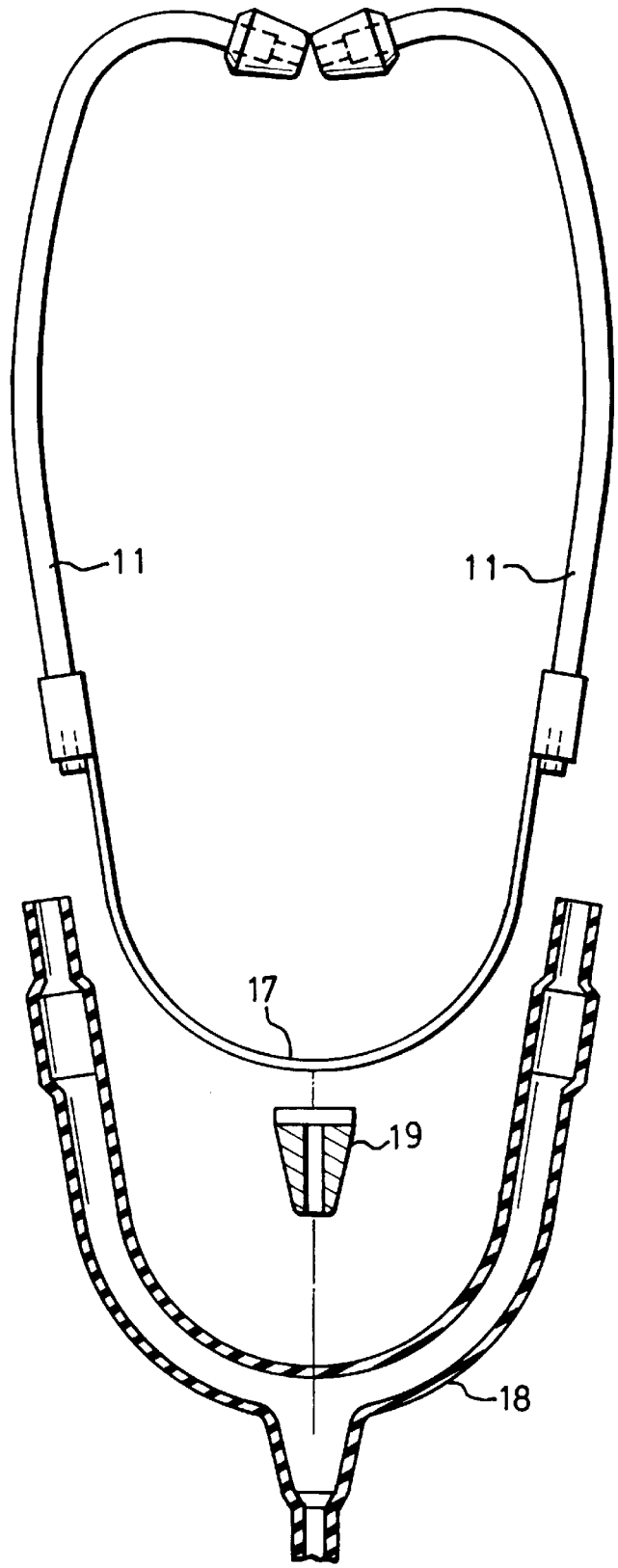
FIG. 3 is an exploded view of another conventional stethoscope.
Figure 4:
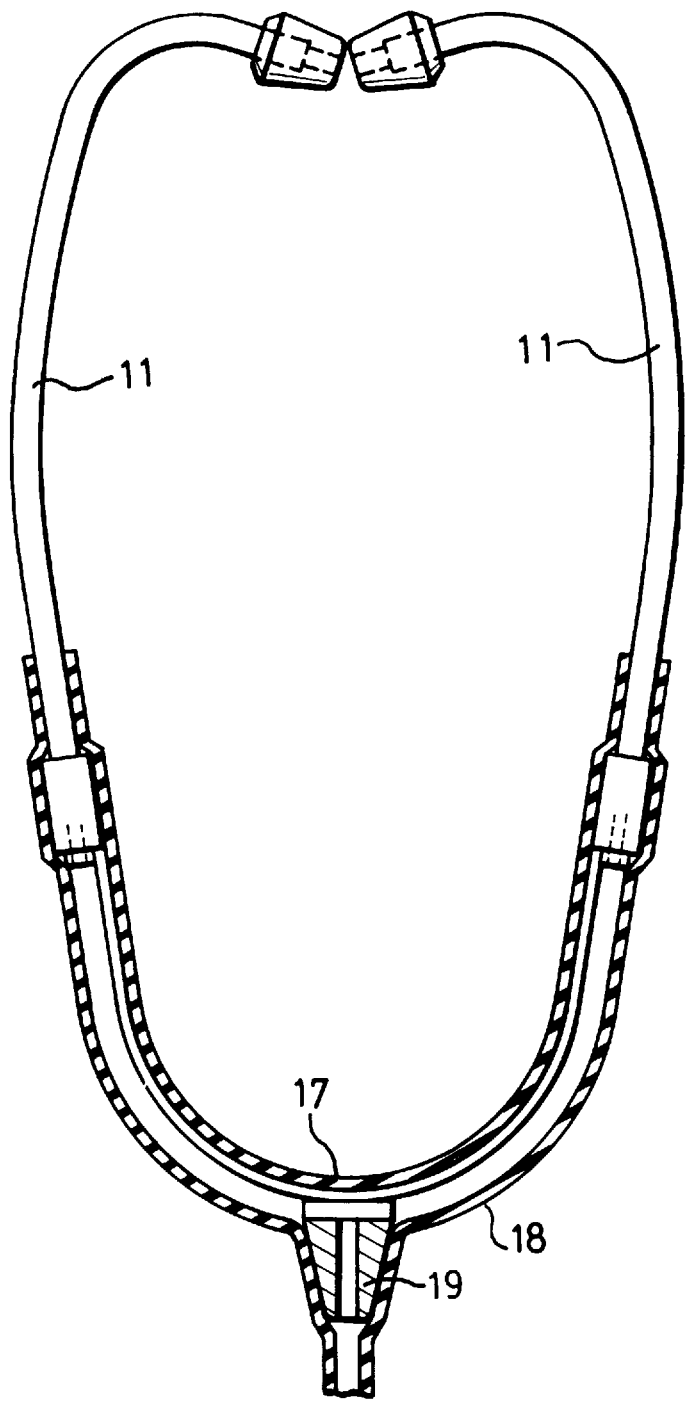
FIG. 4 is a schematic, partly sectional view of the conventional stethoscope of FIG. 3.
Figure 5:
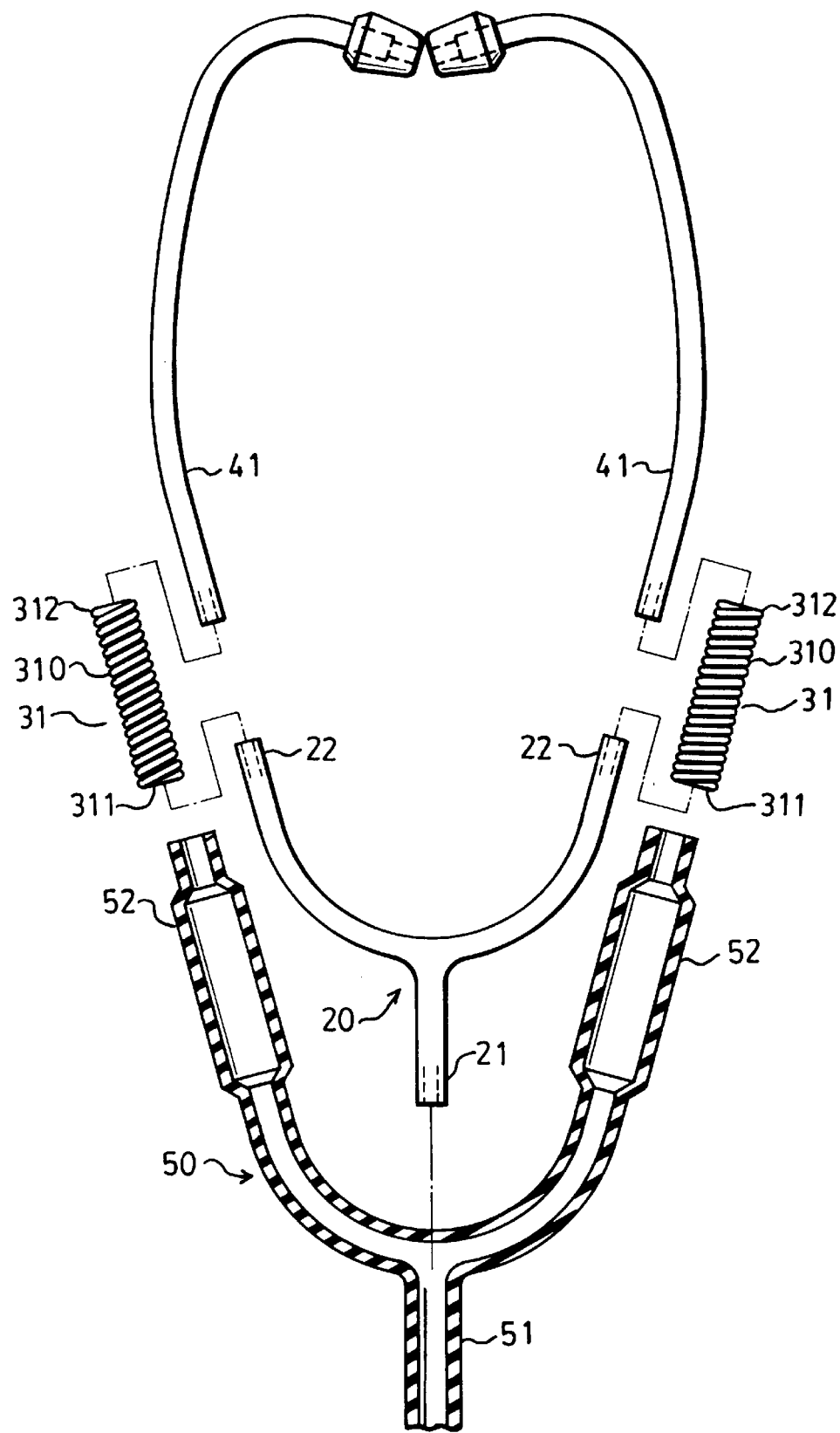
FIG. 5 is an exploded view of a preferred embodiment of a stethoscope according to the present invention.
Figure 6:
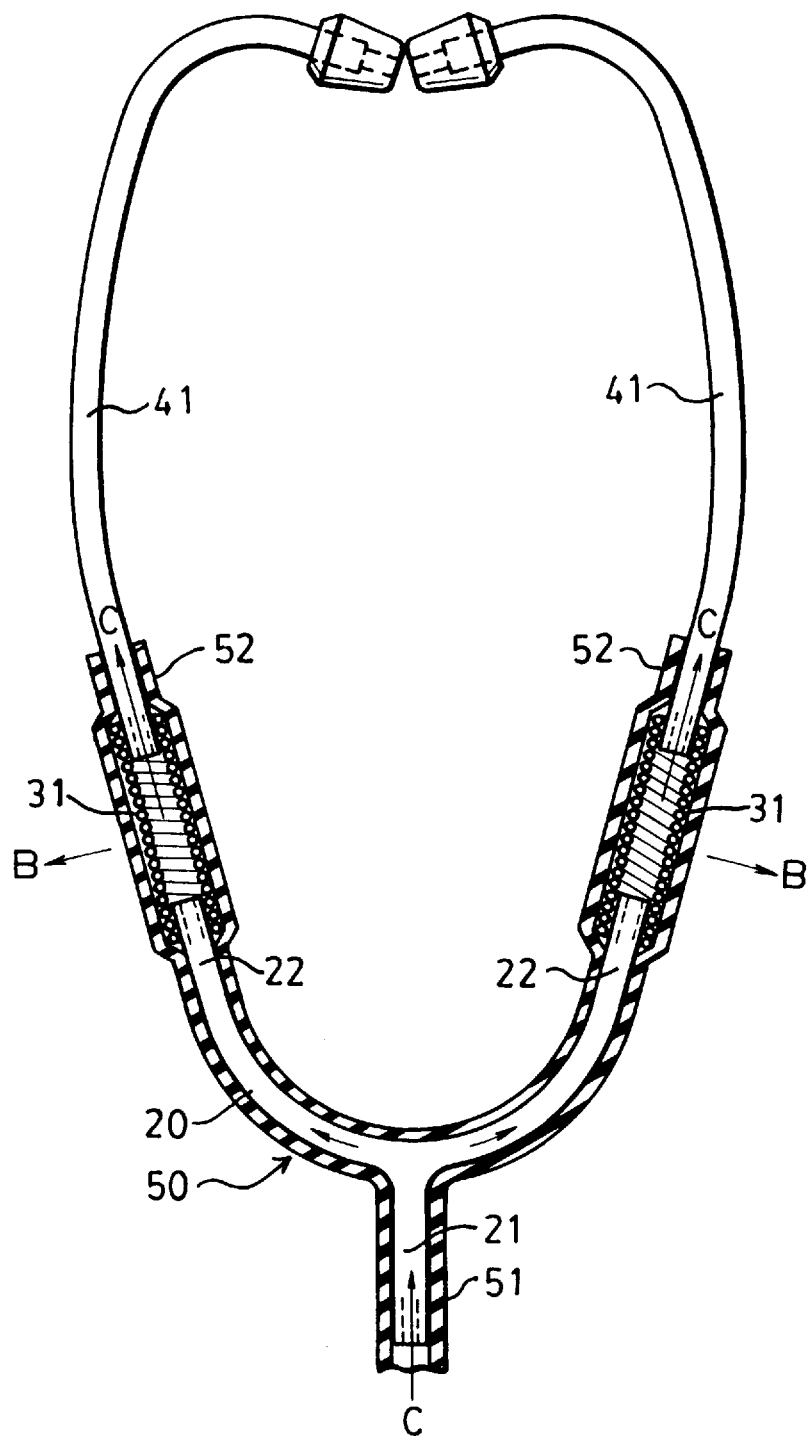
FIG. 6 is a schematic, partly sectional view of the preferred embodiment of the stethoscope according to the present invention.

Referring to FIGS. 5 and 6, a preferred embodiment of a stethoscope according to the present invention is shown to comprise a Y-shaped metal tube 20, a pair of binaural tubes 41, a pair of resilient tubes 31 and a Y-shaped rubber tube 50. The metal tube 20 has a main tube section 21 and two branch tube sections 22 connected to the main tube section 21. Each of the resilient tubes 31 has two opposite ends 311, 312 which connect a distal end of a respective one of the branch tube sections 22 to a distal end portion of a respective one of the binaural tubes 41. Each of the resilient tubes 31 is preferably formed as a coiled spring which has a plurality of coils 310 that are close to one another. The rubber tube 50 has a first tube section 51 which confines the main tube section 21, and two second tube sections 52 connected to the first tube section 51. Each of the second tube sections 52 confines a respective one of the branch tube sections 22, a respective one of the resilient tubes 31 and the distal end portion of a respective one of the binaural tubes 41 in order to conceal the Y-shaped metal tube 20 and the resilient tubes 31 in the Y-shaped rubber tube 50.

With the aforementioned arrangement, in use, an optimum clamping force of the binaural tubes 41 can be applied onto the user's ears due to the optimum spring force of the resilient tubes 31 when the resilient tubes 31 are bent in the directions shown by the arrows B. Therefore, the user of the stethoscope experiences minimum discomfort even after a long period of time. In addition, since the sound can be transmitted smoothly from a chest piece (not shown) through the main tube section 21, the branch tube sections 22 of the metal tube 20, the two resilient tubes 31 and the binaural tubes 41 to the user's ears without encountering any obstruction, as shown by the arrows C, minimum sound distortion is produced.

While the present invention has been described in connection with what is considered the most practical and preferred embodiment, it is understood that this invention is not limited to the disclosed embodiment but is intended to cover various arrangements included within the spirit and scope of the broadest interpretations and equivalent arrangement.

What is claimed is:

1. A stethoscope comprising:

a Y-shaped metal tube having a main tube section and two branch tube sections connected to said main tube section;

a pair of binaural tubes;

a pair of resilient tubes respectively connecting said binaural tubes to said branch tube sections to bias said binaural tubes toward each other, each of said resilient tubes having two opposite ends which connect a distal end of a respective one of said branch tube sections to a distal end portion of a respective one of said binaural tubes; and a Y-shaped rubber tube having a first tube section which confines said main tube section and two second tube sections connected to said first tube section, each of said second tube sections confining a respective one of said branch tube sections, a respective one of said resilient tubes and the distal end portion of a respective one of said binaural tubes in order to conceal said Y-shaped metal tube and said resilient tubes in said Y-shaped rubber tube.

2. The stethoscope as claimed in claim 1, wherein each of said resilient tubes is formed as a coiled spring having a plurality of coils which are close to one another.

3. The stethoscope as claimed in claim 2, wherein said distal end of each of said branch tube sections and said distal end of each of said binaural tubes are inserted into two opposite ends of a respective one of said coiled springs and are spaced from one another.

* * * * *